US012642511B2

(12) United States Patent　　　　(10) Patent No.:　US 12,642,511 B2
Lafond et al.　　　　　　　　　　　(45) Date of Patent:　Jun. 2, 2026

(54) COLOR MAP GENERATION TECHNIQUES FOR SIMULTANEOUSLY DISPLAYING DIFFERENT TYPES OF CAVITATION ACTIVITY ON A DIGITAL IMAGE

(71) Applicant: University of Cincinnati, Cincinnati, OH (US)

(72) Inventors: Maxime Lafond, Cincinnati, OH (US); Kevin Joseph Haworth, Cincinnati, OH (US); Nuria Gonzalez Salido, Cincinnati, OH (US); Christy Katherine Holland, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 594 days.

(21) Appl. No.: 18/013,774

(22) PCT Filed: Jul. 2, 2021

(86) PCT No.: PCT/US2021/040256
§ 371 (c)(1),
(2) Date: Dec. 29, 2022

(87) PCT Pub. No.: WO2022/006499
PCT Pub. Date: Jan. 6, 2022

(65) Prior Publication Data
US 2023/0240663 A1　　Aug. 3, 2023

Related U.S. Application Data

(60) Provisional application No. 63/047,494, filed on Jul. 2, 2020.

(51) Int. Cl.
*G06T 7/90*　　　　(2017.01)
*A61B 8/00*　　　　(2006.01)
*A61B 5/00*　　　　(2006.01)

(52) U.S. Cl.
CPC .............. *A61B 8/5261* (2013.01); *G06T 7/90* (2017.01); *A61B 5/0084* (2013.01); *G06T 2207/10024* (2013.01)

(58) Field of Classification Search
CPC . G06T 7/90; G06T 7/0012; G06T 7/11; G06T 2207/30004; A61B 8/5261; A61B 8/5246; A61B 2034/2063
(Continued)

(56)　　　　　References Cited

U.S. PATENT DOCUMENTS

2010/0056924 A1*　3/2010　Powers ................ A61B 8/0816
　　　　　　　　　　　　　　　　　　　600/458
2011/0067624 A1　　3/2011　Cain et al.
(Continued)

FOREIGN PATENT DOCUMENTS

WO　　WO-2012042423 A1 *　4/2012　........... A61B 17/225

OTHER PUBLICATIONS

Hui Zhong, Junbo Duan, Xuejin Ma, Mingxi Wan, "Pulse Inversion Based Multi-Subharmonic Composite Cavitation Imaging", Oct. 1, 2015 IEEE International Ultrasonics Symposium (IUS) pp. 1-4 (Year: 2015).*
(Continued)

*Primary Examiner* — Jamares Q Washington
(74) *Attorney, Agent, or Firm* — DINSMORE & SHOHL LLP

(57)　　　　　ABSTRACT

A method of simultaneously outputting a plurality of cavitation types on a digital image is provided. The method includes detecting acoustic emissions corresponding to the plurality of cavitation types, the plurality of cavitation types including at least some combination of linear scatter, stable cavitation, and inertial cavitation, generating, based on the acoustic emissions, a two-dimensional color map of the plurality of cavitation types on the digital image, the two-
(Continued)

dimensional color map includes a first acoustic emission corresponding to linear scatter or stable cavitation and a second acoustic emission corresponding to linear scatter or inertial cavitation, and outputting on the digital image, displayed on the display of the computing device, the two-dimensional color map of the plurality of cavitation types.

19 Claims, 8 Drawing Sheets

(58) Field of Classification Search
USPC ................................. 382/128, 130, 131, 132
See application file for complete search history.

(56)                   References Cited

U.S. PATENT DOCUMENTS

| | | | |
|---|---|---|---|
| 2014/0350404 A1 | 11/2014 | Rajguru et al. | |
| 2015/0294497 A1 | 10/2015 | Ng et al. | |
| 2015/0342569 A1* | 12/2015 | Zhai ...................... | G16H 50/30 |
| | | | 600/443 |
| 2019/0209872 A1 | 7/2019 | Staruch et al. | |
| 2019/0329075 A1 | 10/2019 | Sutton et al. | |
| 2022/0011270 A1* | 1/2022 | Arvanitis ............. | G01N 29/348 |
| 2023/0038498 A1* | 2/2023 | Xu ......................... | A61B 34/30 |

OTHER PUBLICATIONS

International Search Report mailed Oct. 5, 2021 in reference to PCT/US2021/40256 filed Jul. 2, 2021.
Written Opinion mailed Oct. 5, 2021 in reference to PCT/US2021/40256 filed Jul. 2, 2021.
EP Extended European Search Report dated May 28, 2024 pertaining to EP application No. 21832229.5 filed Jan. 23, 2023, pp. 1-8.

* cited by examiner

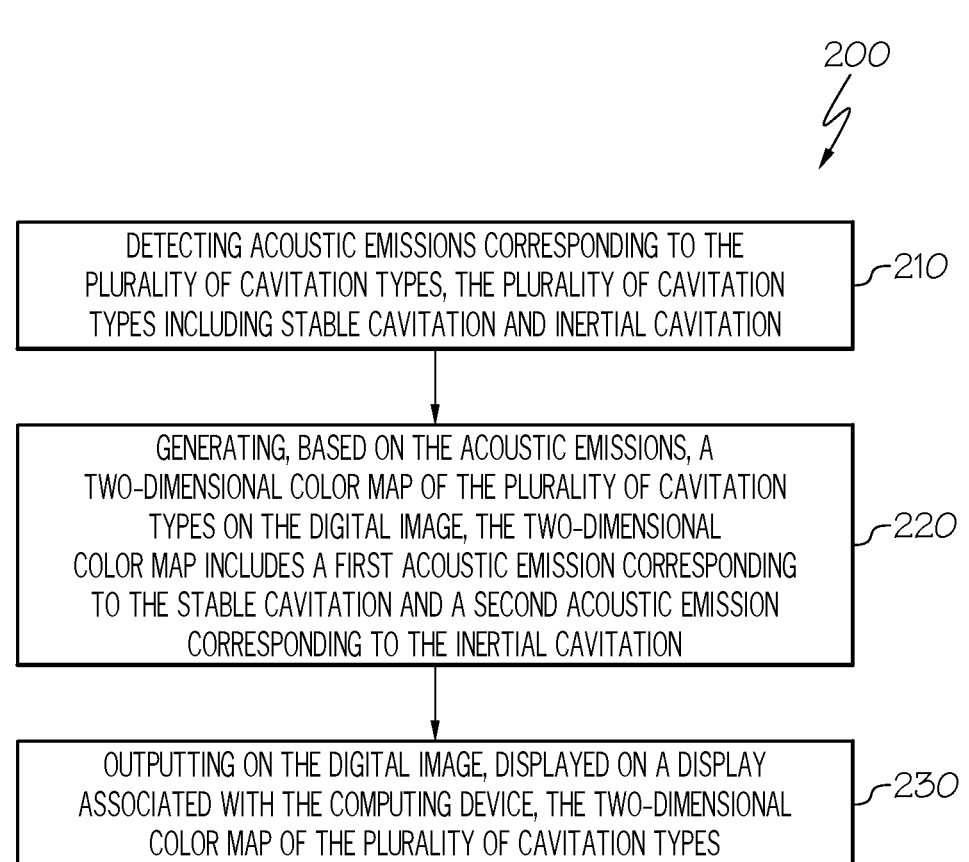

200

| | |
|---|---|
| DETECTING ACOUSTIC EMISSIONS CORRESPONDING TO THE PLURALITY OF CAVITATION TYPES, THE PLURALITY OF CAVITATION TYPES INCLUDING STABLE CAVITATION AND INERTIAL CAVITATION | 210 |

| | |
|---|---|
| GENERATING, BASED ON THE ACOUSTIC EMISSIONS, A TWO-DIMENSIONAL COLOR MAP OF THE PLURALITY OF CAVITATION TYPES ON THE DIGITAL IMAGE, THE TWO-DIMENSIONAL COLOR MAP INCLUDES A FIRST ACOUSTIC EMISSION CORRESPONDING TO THE STABLE CAVITATION AND A SECOND ACOUSTIC EMISSION CORRESPONDING TO THE INERTIAL CAVITATION | 220 |

| | |
|---|---|
| OUTPUTTING ON THE DIGITAL IMAGE, DISPLAYED ON A DISPLAY ASSOCIATED WITH THE COMPUTING DEVICE, THE TWO-DIMENSIONAL COLOR MAP OF THE PLURALITY OF CAVITATION TYPES | 230 |

FIG. 2

COLOR MAP GENERATION TECHNIQUES FOR SIMULTANEOUSLY DISPLAYING DIFFERENT TYPES OF CAVITATION ACTIVITY ON A DIGITAL IMAGE

CROSS REFERENCE TO RELATED APPLICATIONS

This application is a § 371 National Stage Application of International Application No. PCT/US2021/040256 filed on Jul. 2, 2021, and claims benefit of U.S. Provisional Application No. 63/047,494 filed on Jul. 2, 2020, the entire contents of which are herein incorporated by reference.

STATEMENT REGARDING FEDERALLY SPONSORED RESEARCH OR DEVELOPMENT

This invention was made with government support under HL135092 awarded by the National Institutes of Health. The government has certain rights in the invention.

TECHNICAL FIELD

The embodiments described herein generally relate to analyzing and outputting color maps of cavitation activity, and more specifically, to generating and outputting a two-dimensional color map that includes graphical representations of different cavitation types that are simultaneously illustrated on a particular location.

BACKGROUND

A variety of medical therapies and procedures are utilized to generate or mediate certain types of bioeffects. These therapies and procedures, which rely on oscillation bubbles, include drug delivery, thermal ablation, blood barrier disruption, histotripsy, etc. These therapies may be monitored using maps or images of acoustic emissions (or cavitation activity), which may be generated or derived from ultrasound-induced oscillation of bubbles. These emissions may correspond to stable cavitation, inertial cavitation, and so forth. However, the techniques and processes currently utilized for imaging these types of cavitation lack the functionality to illustrate graphical representations of the different types of cavitation, simultaneously on a particular location of a digital image or digital image plane.

Accordingly, a need exists for a cavitation imaging technique that detects acoustic emissions corresponding to different cavitation types and simultaneously illustrates graphical representations of different types of cavitation on a particular portion of a digital image or digital image plane.

SUMMARY

In one embodiment, a method of outputting a plurality of cavitation types on a digital image are contemplated. The method is implemented by a computing device and comprises detecting acoustic emissions corresponding to the plurality of cavitation types, the plurality of cavitation types including stable cavitation and inertial cavitation, generating, based on the acoustic emissions, a two-dimensional color map of the plurality of cavitation types on the digital image, the two-dimensional color map includes a first acoustic emission corresponding to the stable cavitation and a second acoustic emission corresponding to the inertial cavitation, and outputting on the digital image, displayed on a display of the computing device, the two-dimensional color map of the plurality of cavitation types.

In one embodiment, a system for outputting a plurality of cavitation types on a digital image are contemplated. The system may include one or more processors and machine-readable instructions. The machine readable instructions stored in the one or more memory components that cause the system to perform at least the following when executed by the one or more processors: detect acoustic emissions corresponding to a plurality of cavitation types, the plurality of cavitation types including stable cavitation and inertial cavitation, generate, based on the acoustic emissions, a two-dimensional color map of the plurality of cavitation types on a digital image, the two-dimensional color map includes a first acoustic emission corresponding to the stable cavitation and a second acoustic emission corresponding to the inertial cavitation, and output on the digital image, displayed on a display, the two-dimensional color map of the plurality of cavitation types.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 2 depicts a flowchart for outputting a two-dimensional color map of a plurality of cavitation types on a digital image, according to one or more embodiments described and illustrated herein;

DETAILED DESCRIPTION

Figure 1:
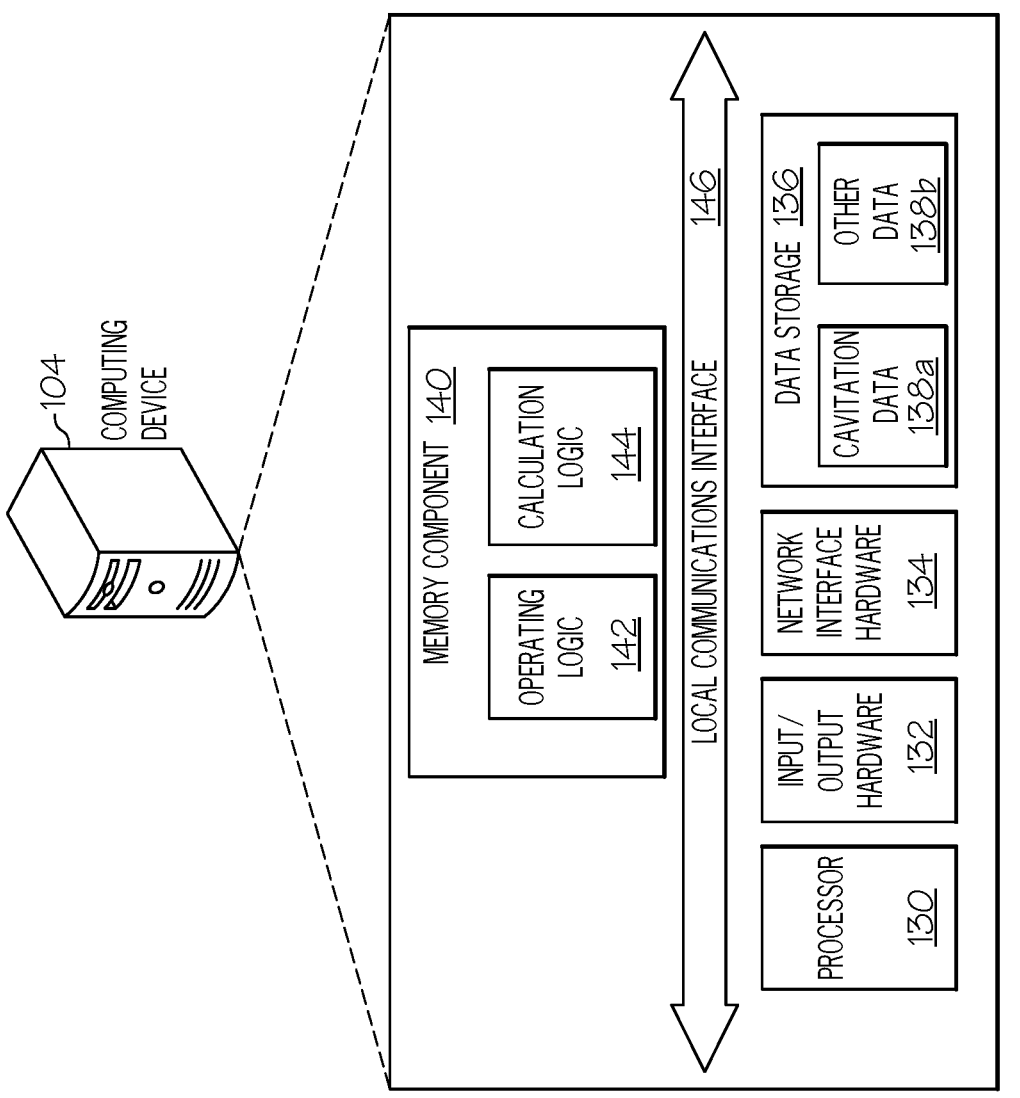
FIG. 1 depicts non-limiting components of a computing environment utilized for generating graphical representations of a plurality of cavitation types on a portion of a digital image or a digital image plane, according to one or more embodiments described and illustrated herein.

As stated, current techniques have features or functionalities that enable the displaying of graphical representations of a single type of cavitation as part of a single image, image map, or image plane, but lack the functionality to simultaneously display graphical representations of different cavitation types (e.g., both stable cavitation and inertial cavitation) on a same location of a digital image map or plane.

The embodiments disclosed herein address and overcome the deficiency present in current techniques. In particular, a method and system as described in the present disclosure are directed to generating and outputting a two-dimensional color map of a plurality of cavitation types on a particular location of a digital image. For example, the method and system as described in the present disclosure detect or capture acoustic emissions corresponding to various types of cavitation, e.g., stable cavitation, inertial cavitation, etc., generate graphical representations corresponding to these separate and distinct types of cavitation, and output these graphical representations using distinct color channels on a particular portion of a digital image.

In embodiments, for the purpose of graphically representing multiple types of cavitation in association with a single pixel or location on a digital image or image plane, a distinct color channel may be designated for each type of cavitation (e.g., stable cavitation and inertial cavitation). Additionally, multiple color channels may be utilized to simultaneously illustrate or display, at a particular pixel or location on the digital image or an image plane, two or more types of cavitation. For example, one type of cavitation may be illustrated using a green channel and another type of cavitation may be illustrated using a red channel. Other colors or color combinations are also contemplated.

In embodiments, when multiple color channels are illustrated on a digital image or image plane, a color combination or color composite may be visible. For example, if a cavitation associated with a green channel and another cavitation associated with a red channel are illustrated or output onto a particular pixel or location on the digital image or image plane, a color composite of the green channel and the red channel may appear on this pixel. Specifically, a yellow graphical representation (a mix of a green and red channels) may be visible. Additionally, the method and system as described in the present disclosure also enables for the determination of a magnitude of an acoustic emission based on an intensity of a color value. For example, variation in the color intensity of one or more graphical representations may enable the determination of the magnitude of the acoustic emission. In embodiments, various techniques, such as the delay, sum, and integration algorithm may be utilized to beamform, or map, the magnitude of acoustic emissions. Other techniques may also be utilized, including, e.g., beamforming the probability of cavitation activity using various statistical methods. Such methods may include phase coherence, amplitude coherence, and so forth.

In embodiments, after detection of acoustic emissions and determination of the magnitudes of acoustic emissions, color channels may be utilized to display graphical representations of the acoustic emissions using various color compositing methodologies. For example, various parameters such as color scheme, dynamic range, scaling such as linear, logarithmic, and other such techniques, compression, and thresholding of a composite image are contemplated. It is also noted that, in embodiments, displaying of the graphical representations corresponding to various types of cavitation may include outputting distinct colors channels associated with these types of cavitation in conjunction with B-mode ultrasound images, or in conjunction with other imaging modalities such as, e.g., Computed Tomography, X-Ray, Magnetic Resonance, Computed Tomography Angiography, Magnetic Resonance Angiography, etc. Displaying such color channels with B-mode ultrasound images may provide useful spatial information related to, e.g., human anatomy. As is described later in this disclosure, outputting distinct color channels and B-mode images (duplexed) together may be done by assigning and adjusting the transparency values associated with the color channels and the B-mode images.

FIG. 1 depicts non-limiting components of a computing environment utilized for generating graphical representations of a plurality of cavitation types on a portion of a digital image or a digital image plane, according to one or more embodiments described and illustrated herein. As illustrated, FIG. 1 includes a computing device 104 which may be a user computing device, a server, a computing device, etc. The computing device 104 includes a processor 130, input/output hardware 132, a network interface hardware 134, a data storage component 136 (which stores cavitation data 138a and/or other data 138b), and a memory component 140. The cavitation data 138a may include data related to stable cavitation, inertial cavitation, and so forth. The other data 138b may include data related to flow rates and flow rate fluctuations of a fluid, pressure data (e.g., hydrodynamic pressure data, etc.), variations in pressure data (e.g., variations in hydrodynamic pressure data), etc.

The memory component 140 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD) (whether local or cloud-based), and/or other types of non-transitory computer-readable medium. Depending on the particular embodiment, these non-transitory computer-readable mediums may reside within the computing device 104 and/or external to the computing device 104.

The memory component 140 may store operating logic 142 and the calculation logic 144. Each of these logic components may include a plurality of different pieces of logic, each of which may be embodied as a computer program, firmware, and/or hardware, as an example. A local interface 146 is also included in FIG. 1 and may be implemented as a bus or other communication interface to facilitate communication among the components of the computing device 104. The processor 130 may include any processing component operable to receive and execute instructions (such as from a data storage component 136 and/or the memory component 140). As described above, the input/output hardware 132 may include and/or be configured to interface with speakers, microphones, and/or other input/output components.

The network interface hardware 134 may include and/or be configured for communicating with any wired or wireless networking hardware, including an antenna, a modem, a LAN port, wireless fidelity (Wi-Fi) card, WiMAX card, mobile communications hardware, and/or other hardware for communicating with other networks and/or devices. From this connection, communication may be facilitated between the computing device 104 and other computing devices. The operating logic 142 may include an operating system and/or other software for managing components of the computing device 104. As discussed above, the operating logic 142 and calculation logic 144 may reside in the memory component 140 and may be configured to cause the processor 130 to perform various calculations, recommend a specific action, initiate generation of graphical representations based on acoustic emissions that correspond to stable cavitation, inertial cavitation, and so forth.

It should be understood that while the components in FIG. 1 are illustrated as residing within the computing device 104, this is merely an example. In some embodiments, one or more of the components may reside external to the computing device 104 or within other devices. It should also be understood that, while the computing device 104 is illustrated as a single device, this is also merely an example. In some embodiments, the operation logic 142 and calculation logic 144 may reside on different computing devices. As an example, one or more of the functionalities and/or components described herein may be provided by the computing device 104. Depending on the particular embodiment, any of these devices may have similar components as those depicted in FIG. 1. To this end, any of these devices may include logic for performing the functionality described herein. Additionally, while the computing device 104 is illustrated with the calculation logic 144 as separate logical components, this is also an example. In some embodiments, a single piece of logic may provide the described function- ality. It should also be understood that while the operating logic 142 and calculation logic 144 are described herein as the logical components, this is also an example. Other components may also be included, depending on the embodiment.

It is further noted that the computing device 104 may be communicatively coupled to a display device, e.g., a moni- tor, a television, and so forth. The graphical representations of the plurality of cavitation types may be output onto the display device such that a graphical representation of stable cavitation and another graphical representation of inertial cavitation may both be simultaneously displayed at the same location (e.g., same pixel) on a digital image or image plane, which is output on the display device.

FIG. 2 depicts a flowchart 200 for outputting a two- dimensional color map of a plurality of cavitation types on a digital image, according to one or more embodiments described and illustrated herein.

In block 210, the computing device 104 is configured to detect acoustic emissions corresponding to a plurality of cavitation types. The plurality of cavitation types include at least stable cavitation and inertial cavitation. As stated, cavitation may be nucleated by stabilized micron-sized bubbles that are injected, e.g., an echocontrast agent or cavitation nucleation agent in a fluid such as blood, etc., and may be induced by ultrasound. Cavitation may be classified under various categories. For example, stable cavitation may refer to a mild or gentle bubble oscillation, while a more violent bubble oscillation and subsequent collapse may be classified as inertial cavitation. As previously stated, a magnitude of a particular type of cavitation may be deter- mined using various techniques, including beamforming a probability of a cavitation activity using statistical tech- niques such as phase coherence and amplitude coherence.

It is noted that determining a magnitude of a cavitation activity and calculating an energy level of a cavitation activity may involve passive cavitation imaging (PCI). It is noted that an example implementation and utilization of a passive cavitation imaging operation or technique is illus- trated in FIG. 3 and described in detail further on in this disclosure. Based on the implementation of the PCI opera- tion and the calculation of an energy calculation of the cavitation activity, a two-dimensional color map, as described in the present disclosure, may be generated and displayed as part of a digital image or plane. It is noted that the acoustic emissions corresponding to the plurality of cavitation types are associated with various frequency bands. Specifically, the acoustic emissions are associated with one or more of a fundamental frequency band, a harmonic frequency band, an inharmonic frequency band, and an ultraharmonic frequency band. Additionally, stable cavitation activity may be associated with an ultraharmonic frequency band and inertial cavitation may be associated with an inharmonic frequency band.

In block 220, the computing device 104 is configured to generate, based on the acoustic emissions, a two-dimen- sional color map of the plurality of cavitation types on the image plane, the two-dimensional color map including a first acoustic emission corresponding to the stable cavitation and a second acoustic emission corresponding to the inertial cavitation. Additionally computing device 104 may also generate a third acoustic emission corresponding to a linear scatter.

In block 230, the computing device 104 may output, on the display, the two-dimensional color map of the plurality of cavitation types on the image plane. The two-dimensional color map may depict each of the first acoustic emission corresponding to stable cavitation and the second acoustic emission corresponding to inertial cavitation with distinct color channels. For example, stable cavitation may be asso- ciated with a first color channel (e.g., a green color channel) and be output as a graphical representation using the first color channel and inertial cavitation may be associated with a second color channel (e.g., a red channel) and be output as a graphical representation using the second color channel. In embodiments, stable cavitation graphical representation using the first color channel and inertial cavitation graphical representation using the second color channel may be output at the same pixel, e.g., simultaneously. It is further noted that the two-dimensional color that is output on the display may also include a linear scatter that corresponds to the third acoustic emission.

Consequently, in embodiments, the computing device 104 may output a mixed graphical representation which may appear as a yellow—a combination of the red channel and the green channel. Additionally, outputting stable cavitation and inertial cavitation graphical representations on a display associated with the computing device 104 may include combining, by the computing device 104, the two-dimen- sional color map with a B-mode ultrasound image. Addi- tionally, the two-dimensional color map may also be com- bined with, e.g., a computed tomography image, an X-ray image, a computed tomography angiography image, a mag- netic resonance image, or a magnetic resonance angiography image. Other such imaging modalities are also contem- plated. In embodiments, combining the two-dimensional color map with a B-mode ultrasound image includes the computing device 104 assigning a first transparency value to the B-mode ultrasound image, and assigning a second transparency value to each of the first color channel (e.g., red channel) and the second color channel (e.g., green channel). In embodiments, the transparency value of the transparency value of the B-mode ultrasound may be lower than each of the first transparency and the second transparency value.

In embodiments, stable cavitation and inertial cavitation graphical representations may overlay a background that includes a B-mode ultrasound image (duplexed). The computing device 104 may then output, on the display associated with computing device 104, the two-dimensional color map in conjunction with the B-mode ultrasound image. In embodiments, the transparency value of the B-mode ultrasound may be lower than each of the second transparency and the third transparency values such that the B-mode ultrasound image, and the entirety of the two-dimensional color map (which may include the first color channel and the second color channel) may be visible on the display. In embodiments, the B-mode ultrasound image may be rendered opaque and the transparency values of the color channels may be modified such that these color channels are partially transparent. For example, transparency values for each pixel may range from a value of 0 (which corresponds to a pixel that is totally transparent) and a value of 0.8 which is associated with a very minor transparency level.

Figure 3:
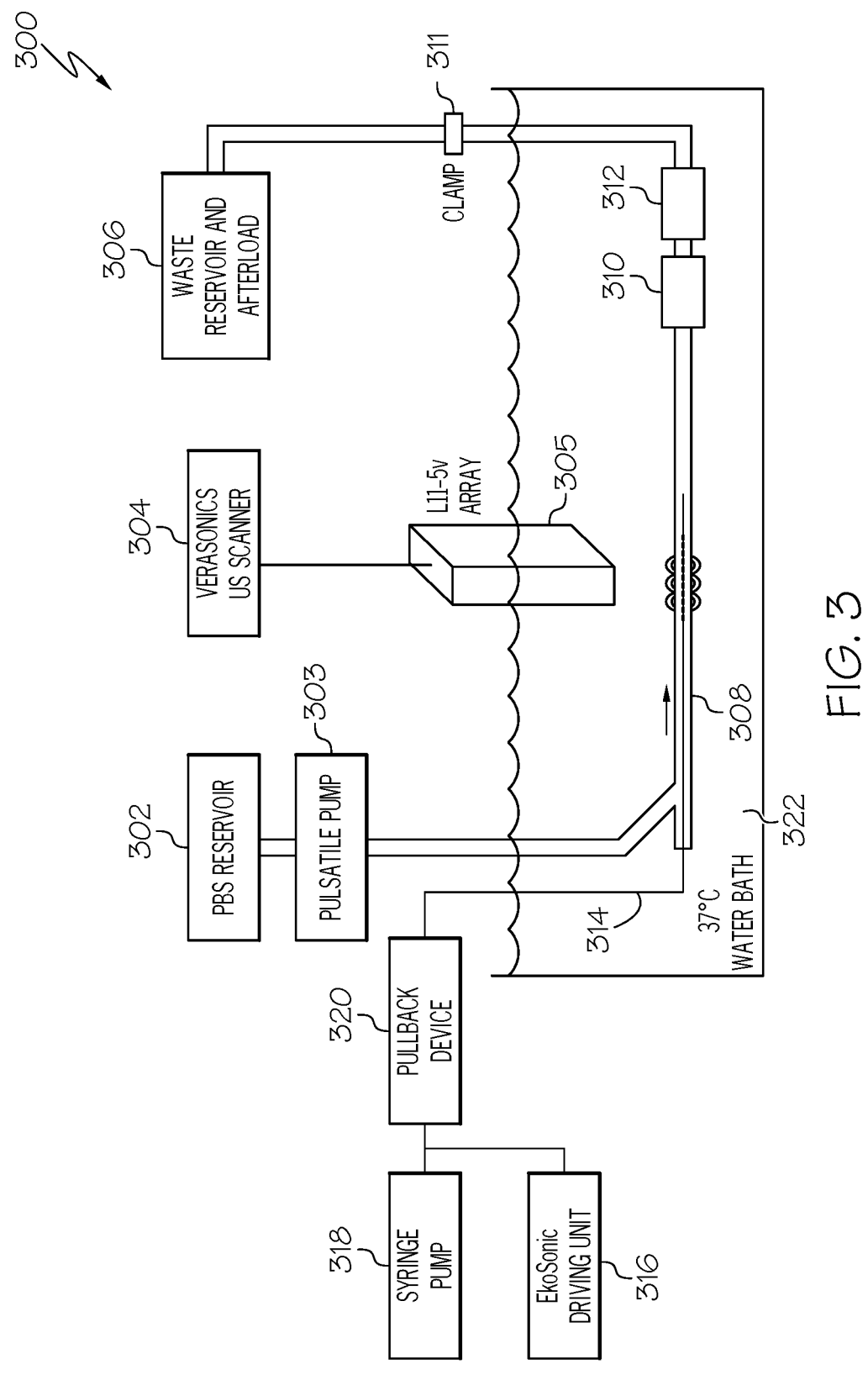
FIG. 3 depicts an example physiological model generated using various components that are utilized to detect cavitation activity, according to one or more embodiments described and illustrated herein.

FIG. 3 depicts an example physiological model generated using various components that are utilized to detect cavitation activity within a fluid, according to one or more embodiments described and illustrated herein. Specifically, FIG. 3 depicts an example experimental component set up for measuring cavitation activity within a fluid. The example physiological model is configured to mimic the characteristics and behaviors of a femoral artery under certain physiological conditions. As illustrated, air-saturated phosphate-buffered saline 322 is stored and maintained in a tank or container. A pulsatile pump 303 may be utilized to transfer the saline from a phosphate-buffered saline (PBS) reservoir 302 via a latex tubing. The saline may be maintained at a temperature of 37° Celsius. The latex tubing may have an inner diameter of 6.35 millimeters. It is noted that the pulsatile pump 303 is a component that serves to replicate flow waveforms for experiments for the purpose of simulating physiological blood flows at numerous points in the body. In embodiments, the pulsatile pump 303 simulates the pumping action of the heart and may include a silicone rubber-covered valves and smooth flow path, which minimizes hemolysis—the rupture or destruction of red blood cells. In embodiments, the pump may output pulses that closely simulate the ventricular action of the heart, thereby providing physiological advantages in blood flow for perfusion in cardiovascular and hemodynamic studies.

Returning to FIG. 3, as part of the physiological model, hydrodynamic pressure of the saline 322 may be measured using a pressure sensor 310 and a flow rate may be measured using a flow sensor 312. The flow sensor that may be connected to a flow meter, both of which operate in conjunction with each other to measure a mass or volumetric fluid flow rate. It is noted that changes in pressure may result from the operation of the pulsatile pump 303, which may be configured to provide a pulsatile flow at various rates and ranges, e.g., from three beats per minute to 200 beats per minute, and an instantaneous flow rate of up to 180 milliliters per second. Other ranges of pulsatile flow rates and displacement volume rates are also contemplated. It is noted that the pulsatile pump parameters (e.g., rate and volume per pulse) and a clamp 311 may be both be adjusted in order to obtain physiological pressure and flow waveforms, each of which may be measured using a pressure meter and a flow meter operating in conjunction with the pressure sensor 310 and the flow sensor 312, respectively. The elevated water and afterload reservoir 306 serves to enable the adjustment of hydrostatic pressure present within the saline 322.

The pressure data and flow data are tracked and captured using one or more computing devices upon which various software applications for fluid flow and pressure variation detection may operate. Additionally, a linear imaging array 305 that is connected to an ultrasound system 304 (e.g., a Versonics US Scanner) may be utilized to obtain B-mode images and acoustic emissions from the saline 322. The B-mode images and acoustics emissions may be beamformed using passive cavitation imaging, which is explained in greater detail in other portions of this disclosure. As illustrated in FIG. 3, the linear imaging array 305 may be positioned in the container storing the saline 322 such that the center of the tube 308 is approximately 22 millimeters within the saline 322, and beyond the focus area of the linear imaging array 305.

A catheter 314 is also placed within the saline 322, and a portion of the catheter 314 is inserted within the tube 308. In particular, in embodiments, the catheter 314 may inserted in the tube 308 (e.g., latex tubing) via a hemostasis valve that is connected to a pullback device 320. In embodiments, the pullback device 320 may be connected to a driving unit 316 and a syringe pump 318. In embodiments, the pull back 320 functions as a component that withdraws a catheter (e.g., the catheter 314) from a particular position in which it is inserted, e.g., from the tube 308. The catheter 314 includes 12 piezoelectric transducer pairs that are spaced 1 centimeter apart all along a specific treatment zone. Specifically, the linear imaging array 305 may be placed axially above the treatment zone or area and be connected to the ultrasound system 304 (e.g., the Versonics US Scanner) for the purpose of the acquisition of the passive cavitation signal.

Figure 5:
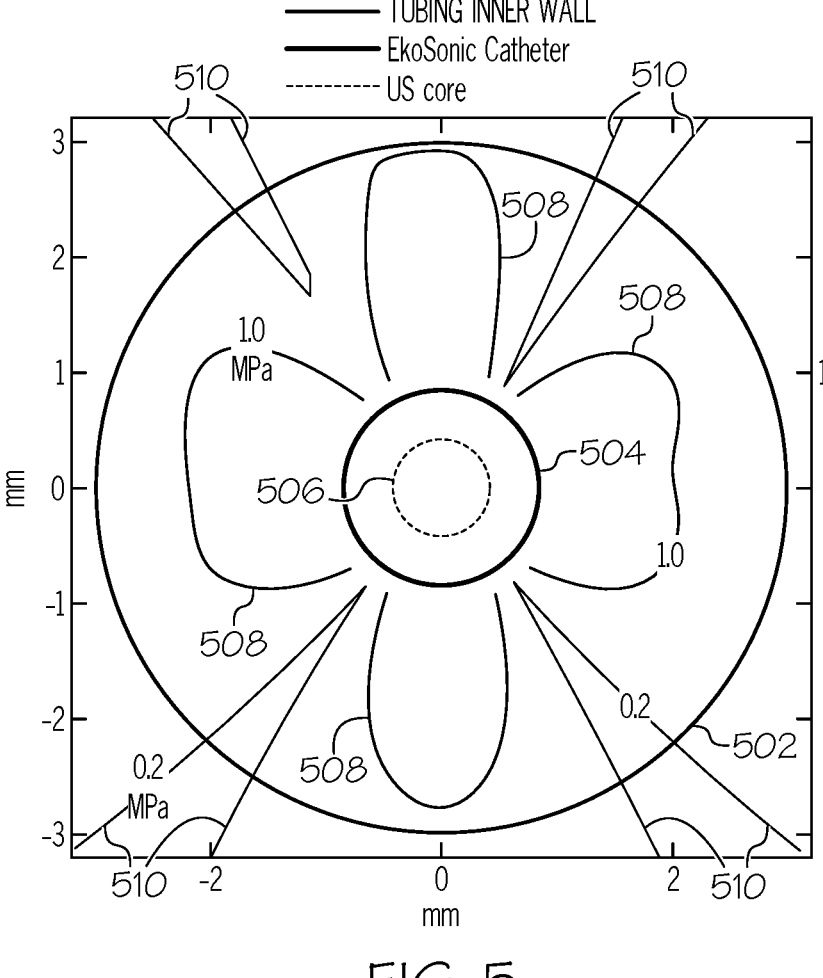
FIG. 5 depicts an example of a pressure field derived from the acoustic pressure output from the transducers within the catheter as a result of actuation of the transducers, according to one or more embodiments described and illustrated herein.

During an example simulation of the various components depicted in FIG. 3, each of the transducers of the catheter 314 may be driven or actuated with 15 millisecond pulses at a pulse repetition frequency of 10 Hz. The temporal peak power associated with these pulses and the pulse repetition frequency may be 9 Watts. Thereafter, the absolute pressure output as a result of the actuation of the transducers may be measured by a hydrophone, which operates to detect acoustic signals in fluids. In other words, a hydrophone (not show in FIG. 2) is utilized to measure, in real time, the absolute pressure output resulting from the actuation (haptic movement or vibration) of the transducers included within the catheter 314. It is noted that the pressure field derived from the acoustic pressure output from the transducers is illustrated in FIG. 5 of the present disclosure. In embodiments, the hydrophone sensitivity or variation may be determined using a custom radiation force balance system that includes an electronic balance and an acoustic absorber that may be calibrated using a traceable transducer. It is further noted that the pressure output that occurs as a result of the actuation of the transducers may be measured azimuthally about the catheter 314 at a fixed distance of 6.0 millimeters from the catheter 314, and the acoustic pressure may also be measured radially from 0.6 millimeters to 56.6 millimeters at a single azimuthal angle over the main lobe of at least one of the transducers. A two-dimensional map of the pressure field derived from the acoustic pressure output from the transducers, which is represented by as a projection of the pressure measurements over a plane, is depicted in FIG. 5 and described in detail later on in this disclosure.

A passive cavitation imaging operation and a cavitation energy calculation operation may be performed, e.g., by the computing device 104, as part of the generation of the example physiological model as illustrated in FIG. 3 and described above. As stated, and with respect to the physiological model illustrated in FIG. 3 and described above, the PCI is used to assess cavitation activity, e.g., caused by the actuation of the transducers by the driving unit 316. With respect to the physiological model of FIG. 3, it is noted that PCI may effectively monitor the spatiotemporal cavitation activity both during a single insonation pulse and throughout infusions, which may occur with the use of or without the use of the pullback device 320. In embodiments, cavitation emissions data may be acquired by the linear imaging array 305 over time periods of 15.1 milliseconds with a sampling frequency of 31.25 MHz. The emissions may be beamformed using the computing device 104 (or a combination of one or more additional computing devices that operate in conjunction with the computing device 104) using one or more software applications, e.g., Matlab.

As stated above, the acquisition of cavitation emission data was initiated based on the actuation of the transducers within the catheter 314. In embodiments, the cavitation emissions data acquired in periods of 15.1 milliseconds may be partitioned into 288 microsecond windows, corresponding to an integer number of acoustic periods at an insonation frequency. The purpose for such partitioning is to minimize spectral leakage. Additionally, it is noted that only 14.4 microseconds of the non-beamformed signal may be processed for the purpose of avoiding the initial 288 microsecond and the final 426 microsecond transients. For each pulse, a respective passive cavitation image may be formed and the energy in the ultraharmonic and inharmonic frequency bands may be integrated throughout the inner spaces of the tube 308.

For examining spatiotemporal cavitation activity within a single 14.4 microsecond processed pulse, the above described processing scheme may be utilized. For example, non-beamformed signals may be partitioned into fifty data sets of 288 microsecond periods or durations and beamformed in accordance with the following equation:

$$E_{BF}\left[n, \vec{r}\right] = \frac{1}{\rho c_0 f_s^2 S_a} \left| \sum_{l=1}^{128} S_l X_l[n] e^{-i2\pi n\Delta f \left| \frac{\vec{r}_l - \vec{r}}{c_0} \right|} \right|^2 - \sum_{l=1}^{128} |S_l X_l[n]|^2, \quad (1)$$

In embodiments, for acquisition of cavitation data, one or more of the transducers within the catheter 314 may be actuated by the driving unit 316. After a temporal delay of 288 microseconds, data sets in durations of 1.44 microseconds may be acquired at a rate of approximately 1 Hz and partitioned into 288 microsecond windows. In embodiments, only the data acquired in the second 288 microsecond window may be processed, primarily because the peak ultraharmonic energy occurred 0.6 milliseconds after the actuation of the transducers by the driving unit 316. It is further noted that PCI is implemented by independent beamforming each cavitation dataset included in each of the 288 microsecond dataset as part of the Fourier domain and integrating the energy in 40 kHz bands at harmonics. Specifically, these include harmonics that may be centered on the multiples of the frequencies of the actuated transducers, fixed at 2.25 MHz $f_0$, ultraharmonics for stable cavitation may be centered on odd multiples of 2.25 MHz/2 (e.g., $f_0$/2), and inharmonic frequencies for inertial cavitation may be centered on multiples of 2.25 MHz/4 (e.g., $f_0$/4) in addition to 35 kHz in order to avoid high order ultraharmonics. In embodiments, the nonlinear behavior of the transducers may indicate that the signal from the harmonics was mainly representative of direct source emissions. In embodiments, it is noted that the energy of cavitation activity per frequency unit, $E_{BF}$, at each location, $\vec{r}$, and discretized frequency index, n, with units of [J V$^2$ Pa$^{-2}$ Hz$^{-1}$], may be calculated using algorithm (1) shown above.

In the above algorithm, the terms $\rho$ and $c_0$ are associated with density and speed of sound values within a media. The term $f_s$ is the sampling frequency, the term $S_a$, is the total area of the imaging array, and the term $S_l$ is the area of the $l^{th}$ element. Additionally, the term $X_l[n]$ is the discrete Fourier-domain signal in volts that is received on the $l^{th}$ element, and the term $\Delta f$ is the frequency step size relating the frequency index n to the frequency such that f=n·$\Delta$f and $\Delta$f corresponds to 31.25 MHz/9000. Finally, the term $\vec{r}_l$ is the vector between the position $\vec{r}$ and the element, l. A summation may be performed over the 128 elements acquired by the linear imaging array 305. Specifically, images may be formed by using algorithm (1) above over particular frequencies of interest and using the following algorithm:

$$E[\vec{r}] = \Delta f \sum_n E_{BF}[n, \vec{r}] \quad (2)$$

Based on algorithm (2), a passive cavitation image pixel amplitude may be expressed as an energy density by scaling $X_l[n]$ by a system calibration factor. For example, using volts per pascal, which includes diffraction and element sensitivity. Additionally it is noted that cavitation images may be graphically represented on a decibel scale relative to 1 J V$^2$/Pa$^2$.

It is further noted that a point spread function (PSF) associated with the algorithm (1) may artifactually attribute energy to locations around an approximate position of various sources. As such, a total energy value of a particular source (e.g., based on cavitation activity) may be inaccurately determined. In embodiments, the beamformed energy may be formed by convolving a true energy source distribution E[n, $\vec{r}$] by the PSF of the beamformer at the position $\vec{a}$ relative to the linear imaging array 305, which may be noted as $A_{PSF}[n, \vec{r}, \vec{a}]$. Various simulations were performed for point sources at various locations within the tube 308 and it was determined that average beamformed energy within a particular region of interest varied from the true energy by a maximum tolerance level of approximately less than or greater than 10 percent at a frequency value of 2 MHz and less than or greater than 18 percent at a frequency value of 8 MHz. As such, these error percentages compensated for each other such that the average calculated variations were less than 1 percent.

Because of this relatively small variation, the PSF function was approximated to be independent of the source location such that $A_{PSF}[n, \vec{r}, \vec{a}]$ was set as being equal to $A_{PSF}[n, \vec{r} - \vec{a}]$. Additionally, the cavitation within the tube 308 is determined to be sufficiently spatially uniform such that any error induced by a spatial invariance of the PSF may be neglected. In embodiments, the beamformed energy may be expressed as:

$$E_{BF}[n, \vec{r}] = A_{PSF}[n, \vec{r} - \vec{a}] * E[n, \vec{r}], \quad (3)$$

In algorithm (3), the term, $\vec{r}$ may be written as:

$$\int_{-\infty}^{+\infty} E_{BF}[n, \vec{r}]d\vec{r} = \int_{-\infty}^{+\infty} A_{PSF}[n, \vec{x}]d\vec{x} \cdot \int_{-\infty}^{+\infty} E[n, \vec{y}]d\vec{y} \tag{4}$$

In algorithm (4), as the cavitation based energy sources are micro-bubbles that are smaller than a wavelength, these sources may be considered point sources. As such, under this condition, the integral of the true energy field may be equal to the total energy, E[n], at frequency index, n. The total energy E[n] may be determined using the following algorithm:

$$E[n] = \frac{\int E_{BF}[n, \vec{r}]d\vec{r}}{\int A_{PSF}[n, \vec{x}]d\vec{x}}. \tag{5}$$

To determine total energy, an integration of the beamformed energy may be calculated over a particular region of interest, which may be denoted as $R_{BF}$. The term $R_{BF}$ includes the tube lumen and a boundary that is sufficiently large to account for the spread of energy due to the PSF. Specifically, in the physiological model illustrated in FIG. 3 and described above, the boundary may be two millimeters and four millimeters in the lateral and axial directions. It is noted that though $\vec{r}$ may be treated as a continuous variable, algorithm (5) may have to be discretized for the purpose of displaying images. The discretized form of $\vec{r}$ and $\vec{x}$ may be noted as $\vec{r}_d$ and $\vec{x}_d$. Additionally, discretization over various calculation grids for the PSF and the beamformed image yields the following algorithm:

$$E[n] = \frac{\Delta\vec{r}\sum_{\vec{r}_d}^{\vec{r}_d \in R_{BF}} E_{BF}[n, \vec{r}_d]}{\Delta\vec{x}\sum_{\vec{x}_d}^{\vec{x}_d \in R_{PSF}} A_{PSF}[n, \vec{x}_d]}, \tag{6}$$

In the above algorithm, $\Delta\vec{r}$ and $\Delta\vec{x}$ are representative of a pixel size of the beamformed image and a simulated point spread function, respectively. The pixel sizes are assumed to be significantly smaller than a −3 dB area of the PSF. Relating to algorithm (6), the denominator is the sum of the amplitudes of the pixels in the point spread function, which may be represented as $$\Delta\vec{x}\sum_{\vec{x}_d}^{\vec{x}_d \in R_{PSF}} A_{PSF}[n, \vec{x}_d].$$

This may be calculated at discrete frequencies between 0.5 and 12 MHz and be configured to fit an equation of having the variables of C/f. In such an equation, the term C relates to a fitting parameter and the term f relates to a frequency. The fitting parameter may be determined to be $17.68 \times 10^6$ Hz/m². Based on this value, and by replacing the denominator in Algorithm (6) with the equation of C/f, a total cavitation energy, $E_{tot}$, within the tube 308 may be determined using the following algorithm:

$$E_{tot} = \Delta f \sum_n E[n] = \sum_n \frac{\Delta\vec{r}\sum_{\vec{r}_d}^{\vec{r}_d \in R_{BF}} E_{BF}[n, \vec{r}_d]}{17.68 \times 10^6} \cdot n\Delta f^2. \tag{7}$$

Figure 4A:
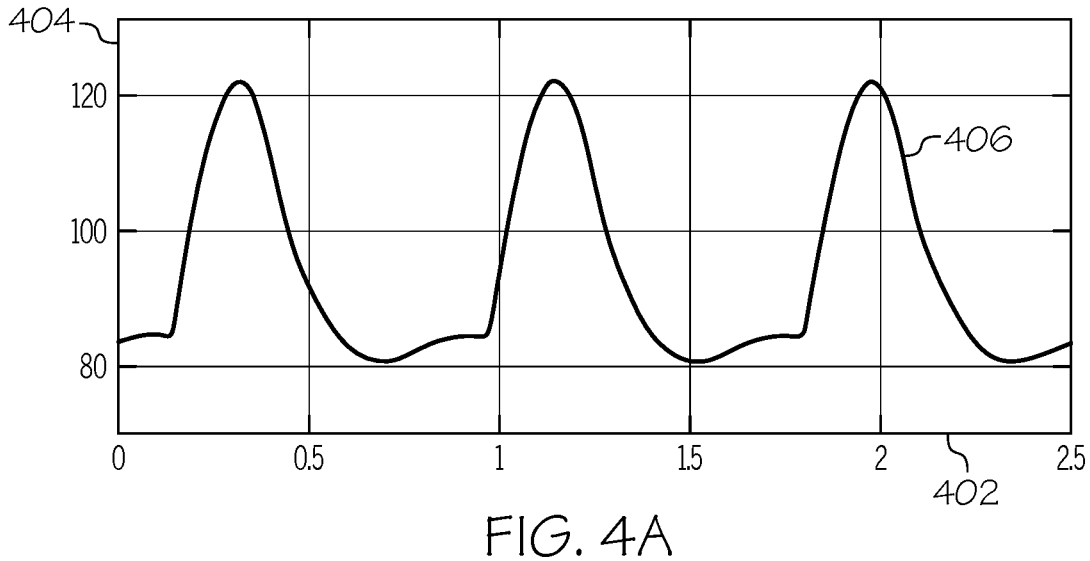
FIG. 4A depicts a graphical representation of pressure measurement based on certain flow conditions.

FIG. 4A depicts a graphical representation 406 of pressure measurement based on certain flow conditions. Specifically, FIG. 4A depicts a graphical representation in which an x-axis 402 corresponds to time values measured in seconds and a y-axis 404 corresponds to pressure values measured in mmHG or millimeters of mercury (i.e. measurement of pressure inside a fluid). As illustrated, pressure values derived as a result of the actuation of the transducers (as described above with respect to FIG. 3) include a peak value of 122 mmHG. It is noted that, depending on the variation in the extent of the actuation of the transducers, the pressure values may be higher or lower.

Figure 4B:
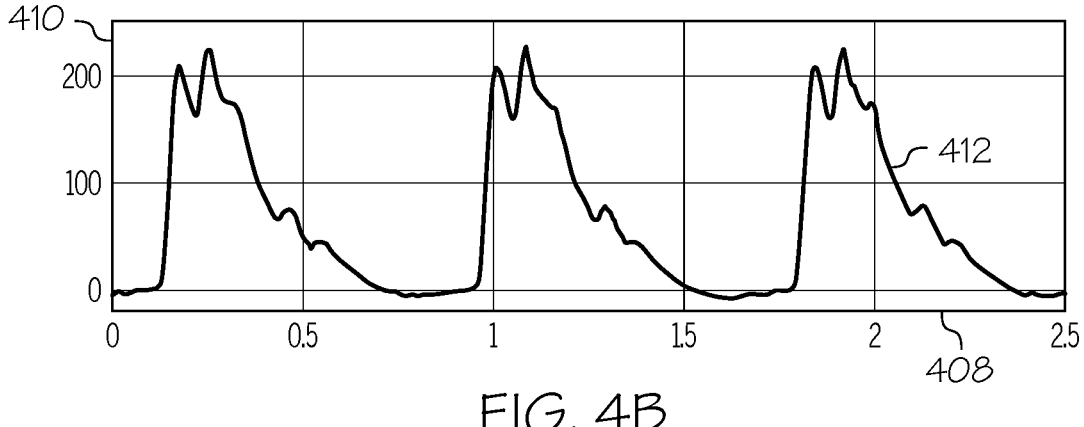
FIG. 4B depicts a graphical representation flow rate measurement based on certain flow conditions.

FIG. 4B depicts a graphical representation 412 of flow rate measurement based on certain flow conditions. Specifically, FIG. 4B depicts a graphical representation in which another x-axis 408 corresponds to time values measured in seconds and another y-axis 410 corresponds to flow rate values measured in milliliters per minute. As illustrated, flow rate values derived as a result of the actuation of the transducers (as described above with respect to FIG. 3) include a peak value of approximately 200 milliliters per minute.

FIG. 5 depicts an example of a pressure field derived from the acoustic pressure output from the transducers within the catheter 314 as a result of actuation of the transducers, according to one or more embodiments described and illustrated herein. Specifically, FIG. 5 depicts a graphical representation of a directivity pattern and a peak rarefactional pressure field of the catheter 314, which may be generated from a pair of ultrasound core transducers located within the catheter 314. The catheter 314 is represented by a catheter-representation 504 and the ultrasonic core transducers are represented by the dotted lines 506. These core transducers may be located within the tube 308, as describe above. The perimeter of the tube 308 may be represented by the larger circular line 502. Additional, the straight lines 510 the curved lines 508 correspond to rarefactional acoustic pressure isolines associated with 0.2 MPa and 1.0 MPa. The values of 02 and 1.0 MPa are the predicted rarefactional pressure threshold values for stable and inertial cavitation.

Figure 6:
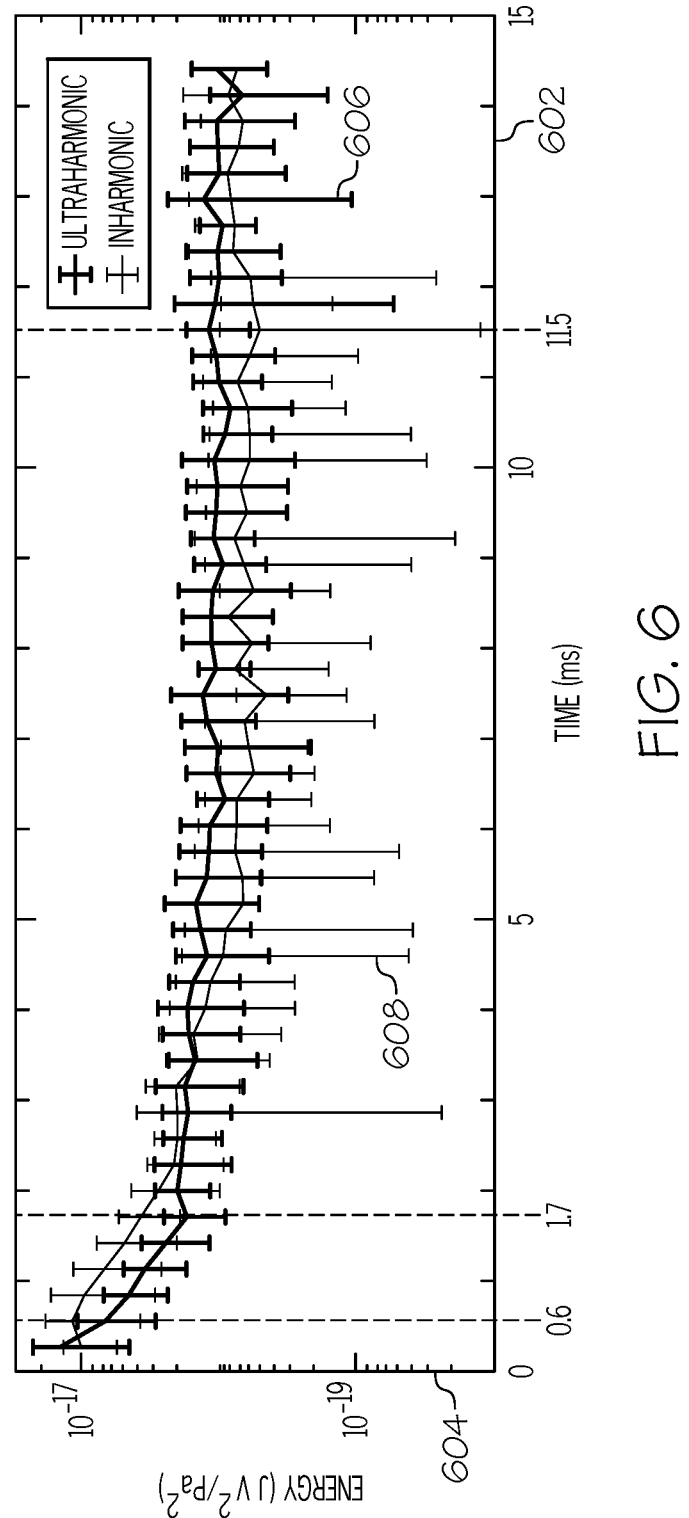
FIG. 6 depicts an example graphical representation of cavitation energy values determined as a result of various calculations performed as described in the present disclosure, according to one or more embodiments described and illustrated herein.

FIG. 6 depicts an example graphical representation of cavitation energy values determined as a result of various calculations performed as described in the present disclosure, according to one or more embodiments described and illustrated herein. As illustrated, FIG. 6 depicts a graphical representation in which an x-axis 602 corresponds to time values represented in milliseconds and a y-axis 604 corresponds to energy values represented by $JV^2/Pa^2$. Markers 606, as depicted, correspond to inharmonic frequency bands as a function of time during an insonation pulse that spans from a time period of approximately 0.3 milliseconds to 14.4 milliseconds. Additionally marker 608, as depicted, correspond to ultraharmonic frequency bands as a function of time during an insonation pulse that spans from a time period of approximately 0.3 milliseconds to 14.4 milliseconds. The inharmonic frequency bands and the ultraharmonic frequency bands reduce by an order of magnitude during the first three milliseconds of the insonation pulse and then plateau from three milliseconds to approximately 14.4 milliseconds. The graphical representation depicted in FIG. 6 includes ultraharmonic and inharmonic frequency bands corresponding to ultraharmonic and inharmonic acoustic emissions with seven pulses at a pulse repetition frequency of 10 Hz. Each of the seven pulses is a 15 millisecond pulse. Additionally, it is noted that time points 0.6 milliseconds, 1.7 milliseconds, and 11.5 milliseconds are marked with dashed lines.

It is noted that FIG. 6 illustrates spatiotemporal graphical representations of stable and inertial cavitation based on the driving unit 316 activating the transducers within the catheter 314 with a power value of 9 W. Additionally, it is noted that, as illustrated in FIG. 6, cavitation energy decreased by one order of magnitude over the first 3 milliseconds of the 15-millisecond pulse for both the stable and inertial cavitation activity. Stable cavitation activity corresponds to the ultraharmonic frequency band and inertial cavitation activity corresponds to the inharmonic frequency band.

Figure 7A:
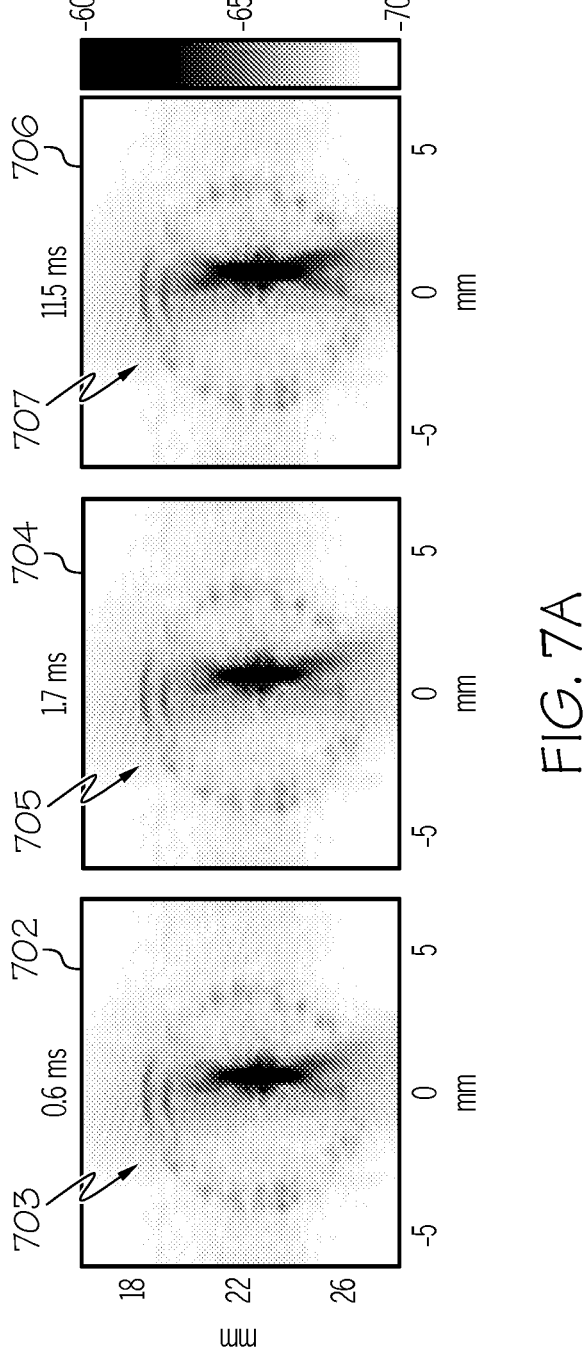
FIG. 7A depicts images of harmonic energy levels of cavitation emissions corresponding to various time periods, according to one or more embodiments described and illustrated herein.

FIG. 7A depicts images of harmonic energy levels of cavitation emissions corresponding to various time periods, according to one or more embodiments described and illustrated herein. Specifically, FIG. 7A depicts harmonic energy images 702, 704, and 706, which correspond to time periods of 0.6 microseconds, 1.7 microseconds, and 11.5 microseconds, respectively. As illustrated, harmonic graphical representations 703, 705 and 707 illustrate dark portions in the center of the harmonic energy images 702, 704, and 706. These dark portions correspond to signals from the transducers located within the tube 308, as illustrated in FIG. 3 and described above. It is further noted that the harmonic graphical representations, 703, 705 and 707 are illustrated with partial transparency while the background, which may be an ultrasound image, is illustrated without transparency. However, in other embodiments, the harmonic graphical representations, 703, 705 and 707 may be illustrated as having higher transparency values and the ultrasound image may be depicted as opaque. Other permutations and combinations are also contemplated. It is noted that the two-dimensional map depicted in 7A may be a two-dimensional color may that represents values using decibels (dB) relative to various energy values, e.g., represented by J $V^2/Pa^2$.

Figure 7B:
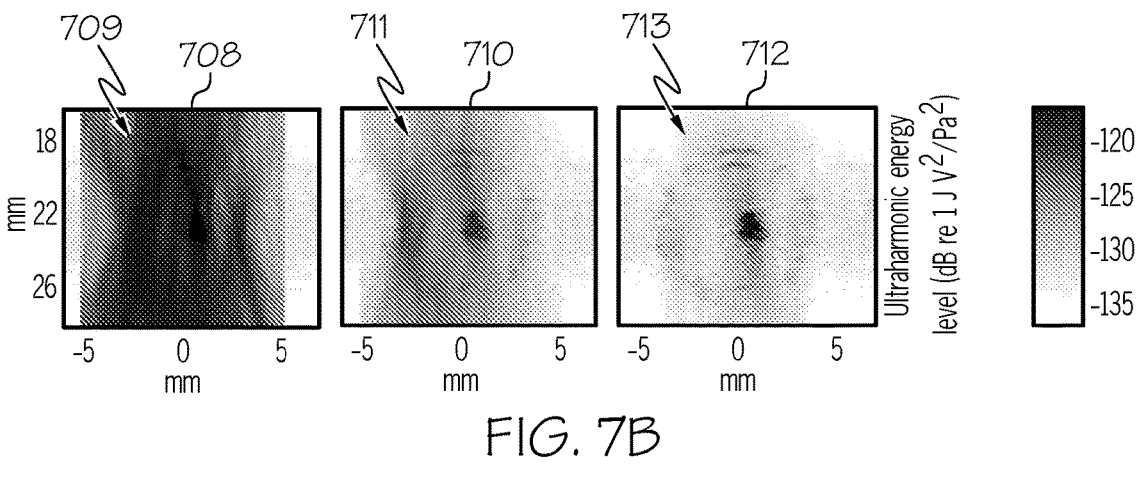
FIG. 7B depicts images of ultraharmonic energy levels of cavitation emissions corresponding to various time periods, according to one or more embodiments described and illustrated herein.

FIG. 7B depicts images of ultraharmonic energy levels of cavitation emissions corresponding to various time periods, according to one or more embodiments described and illustrated herein. Specifically, FIG. 7B depicts ultraharmonic energy images 708, 710, and 712, which correspond to time periods of 0.6 microseconds, 1.7 microseconds, and 11.5 microseconds, respectively. As illustrated, ultraharmonic graphical representations 709, 711, and 713 illustrate dark portions (e.g., green color) in various parts of the ultraharmonic energy images 708, 710, and 712. These dark portions correspond to signals associated with stable cavitation activity. It is further noted that the ultraharmonic graphical representations, 709, 711 and 713 are illustrated with partial transparency while the background, which may be an ultrasound image, is illustrated without transparency. However, in other embodiments, the ultraharmonic graphical representations, 709, 711 and 713 may be illustrated as having higher transparency values and the ultrasound image may be depicted as opaque. In embodiments, when the ultraharmonic graphical representations 709, 711, and 713 are output onto a display associated with the computing device 104, these representations may be displayed using a green color channel.

Figure 7C:
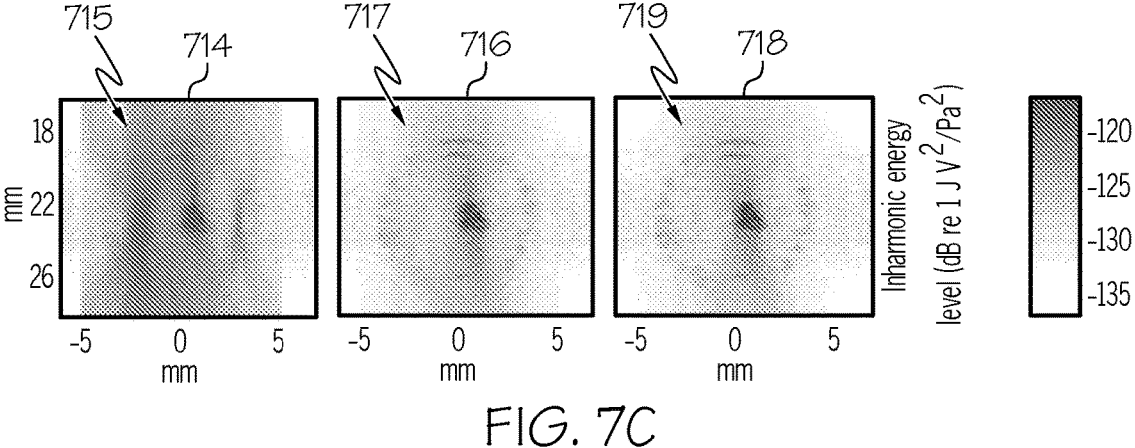
FIG. 7C depicts images of inharmonic energy levels of cavitation emissions corresponding to various time periods, according to one or more embodiments described and illustrated herein.

FIG. 7C depicts images of inharmonic energy levels of cavitation emissions corresponding to various time periods, according to one or more embodiments described and illustrated herein. Specifically, FIG. 7C depicts inharmonic energy images 714, 716, and 718, which correspond to time periods of 0.6 microseconds, 1.7 microseconds, and 11.5 microseconds, respectively. As illustrated, inharmonic graphical representations 715, 717, and 719 illustrate dark portions (e.g., red color) in various parts of the inharmonic energy images 714, 716, and 718. These dark portions correspond to signals associated with inertial cavitation activity. It is further noted that the inharmonic graphical representations, 715, 717, and 719 are illustrated with partial transparency while the background, which may be an ultrasound image, is illustrated without transparency. However, in other embodiments, the inharmonic graphical representations, 715, 717, and 719 may be illustrated as having higher transparency values and the ultrasound image may be depicted as opaque. In embodiments, when the inharmonic graphical representations 715, 717, and 719 are output onto a display associated with the computing device 104, these representations may be displayed using a red color channel.

Figure 7D:
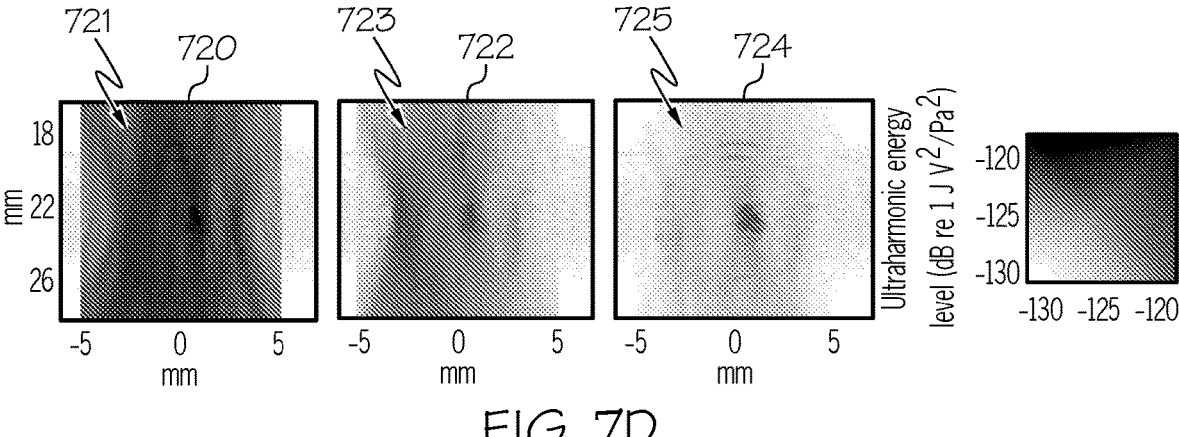
FIG. 7D depicts images of a mixture of inharmonic and ultraharmonic energy levels depicted in FIGS. 7B and 7C.

FIG. 7D depicts images of a mixture of inharmonic and ultraharmonic energy levels as depicted in FIGS. 7B and 7C. As illustrated, a graphical representation 721 in mixed energy image 720 represents a mixture of the ultraharmonic energy level included in the ultraharmonic graphical representation 709 with the inharmonic energy level included in the inharmonic graphical representation 715. The graphical representation 723 in mixed energy image 722 represents another mixture of the ultraharmonic energy level included in the ultraharmonic graphical representation 711 with the inharmonic energy level included in the inharmonic graphical representation 717. Additionally, the graphical representation 725 in mixed energy image 724 represents another mixture of the ultraharmonic energy level included in the ultraharmonic graphical representation 712 with the inharmonic energy level included in the inharmonic graphical representation 718. In embodiments, when the graphical representations 721, 723, and 725 are output onto a display associated with the computing device 104, these representations may be displayed yellow—a mix of the red and green color channels. Because the graphical representations 721, 723, 725 includes ultraharmonic graphical representations associated with stable cavitation activity and inharmonic graphical representation associated with inertial cavitation, the present system simultaneously displays graphical representations of different types of cavitation (e.g., both stable cavitation and inertial cavitation) in a single image of a region of interest.

It should also be understood that the embodiments described herein relate to a method of simultaneously outputting a plurality of cavitation types on an image plane is provided. The method includes detecting acoustic emissions corresponding to the plurality of cavitation types, the plurality of cavitation types including at least stable cavitation and inertial cavitation, generating, based on the acoustic emissions, a two-dimensional color map of the plurality of cavitation types on the image plane, the two-dimensional color map includes a first acoustic emission corresponding to stable cavitation and a second acoustic emission corresponding to inertial cavitation, and outputting, on the display of the computing device, the two-dimensional color map of the plurality of cavitation types on the image plane. It should be further understood that the embodiments described herein relate to a system of simultaneously outputting a plurality of cavitation types on an image plane. The system includes one or more processors, one or more memory components communicatively coupled to the one or more processors, and machine readable instructions stored in the one or more memory components that cause the system to perform at least the following when executed by the one or more processors: detect acoustic emissions corresponding to a plurality of cavitation types, the plurality of cavitation types including at least stable cavitation and inertial cavitation, generate, based on the acoustic emissions, a two-dimensional color map of the plurality of cavitation types on an image plane, the two-dimensional color map includes a first acoustic emission corresponding to stable cavitation and a second acoustic emission corresponding to inertial cavitation, and output, on a display, the two-dimensional color map of the plurality of cavitation types on the image plane.

The terminology used herein is for the purpose of describing particular aspects only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A method of outputting a plurality of cavitation types on a digital image, the method being implemented by a computing device, the method comprising:

detecting acoustic emissions corresponding to the plurality of cavitation types, the plurality of cavitation types comprising stable cavitation and inertial cavitation;

generating, based on the acoustic emissions, a two-dimensional color map of the plurality of cavitation types on the digital image, the two-dimensional color map comprising a first acoustic emission corresponding to the stable cavitation and a second acoustic emission corresponding to the inertial cavitation;

associating a first color channel with the stable cavitation and associating a second color channel with the inertial cavitation; and outputting on the digital image, displayed on a display associated with the computing device, the two-dimensional color map of the plurality of cavitation types, wherein the first color channel and the second color channel are output simultaneously at a respective location on the digital image when the first acoustic emission and the second acoustic emission are detected at the respective location on the digital image.

2. The method of claim 1, wherein the plurality of cavitation types comprises a linear scatter.

3. The method of claim 1, further comprising combining, by the computing device, the two-dimensional color map outputted on the digital image with a B-mode ultrasound image.

4. The method of claim 3, wherein the combining comprises:

assigning a first transparency value to the B-mode ultrasound image; and assigning a second transparency value to the digital image.

5. The method of claim 4, wherein the first transparency value is lower than the second transparency value.

6. The method of claim 3, further comprising outputting, on the display of the computing device, combination of the two-dimensional color map and the B-mode ultrasound image.

7. The method of claim 2, wherein the acoustic emissions are associated one or more of fundamental, harmonic, inharmonic, and ultraharmonic frequency bands.

8. The method of claim 7, wherein the stable cavitation is associated with an ultraharmonic frequency band.

9. The method of claim 7, wherein the stable cavitation is associated with a harmonic frequency band.

10. The method of claim 7, wherein the inertial cavitation is associated with an inharmonic frequency band.

11. The method of claim 7, wherein the linear scatter is associated with a harmonic frequency band.

12. The method of claim 7, wherein the linear scatter is associated with a fundamental frequency band.

13. The method of claim 1, further comprising combining, by the computing device, the two-dimensional color map with a computed tomography image, an X-ray image, a computed tomography angiography image, a magnetic resonance image, or a magnetic resonance angiography image.

14. The method of claim 1, wherein the digital image is based on planar data.

15. The method of claim 1, wherein the digital image is based on volumetric data.

16. The method of claim 2, further comprising generating the two-dimensional color map to include a third acoustic emission corresponding to the linear scatter.

17. A system comprising:

one or more processors;

one or more memory components communicatively coupled to the one or more processors; and machine readable instructions stored in the one or more memory components that cause the system to perform at least the following when executed by the one or more processors:

detect acoustic emissions corresponding to a plurality of cavitation types, the plurality of cavitation types comprising stable cavitation and inertial cavitation, generate, based on the acoustic emissions, a two-dimensional color map of the plurality of cavitation types on a digital image, the two-dimensional color map comprising a first acoustic emission corresponding to the stable cavitation and a second acoustic emission corresponding to the inertial cavitation, associate a first color channel with the stable cavitation and associate a second color channel with the inertial cavitation, and output on the digital image, displayed on a display, the two-dimensional color map of the plurality of cavitation types, wherein the first color channel and the second color channel are output simultaneously at a respective location on the digital image when the first acoustic emission and the second acoustic emission are detected at the respective location on the digital image.

18. The system of claim 17, wherein the plurality of cavitation types comprises a linear scatter.

19. The system of claim 17, wherein the acoustic emissions are associated one or more of fundamental, harmonic, inharmonic, and ultraharmonic frequency bands.

\* \* \* \* \*